US006570069B1

United States Patent
Hammock et al.

(10) Patent No.: US 6,570,069 B1
(45) Date of Patent: May 27, 2003

(54) NUCLEIC ACIDS ENCODING PLANT INHIBITORS OF APOPTOSIS AND TRANSGENIC CELLS AND PLANTS EXPRESSING THEM

(75) Inventors: Bruce D. Hammock, Davis, CA (US); Qihong Huang, Davis, CA (US); Susumu Maeda, deceased, late of Davis, CA (US), Hiroko Maeda, executor

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/502,528

(22) Filed: Feb. 10, 2000

(51) Int. Cl.[7] .......................... A01H 5/00; C12N 15/00; C12N 15/12; C12N 15/82; C12N 15/866
(52) U.S. Cl. .................. 800/298; 424/93.2; 435/320.1; 435/419; 536/23.5
(58) Field of Search ............................... 536/23.1, 23.5; 435/320.1, 419, 348, 235.1; 800/298; 424/93.2

(56) References Cited

U.S. PATENT DOCUMENTS 6,162,965 A * 12/2000 Hansen

FOREIGN PATENT DOCUMENTS

| WO | WO 98 53091 A | 11/1998 |
|---|---|---|
| WO | WO 98 54961 A | 12/1998 |

OTHER PUBLICATIONS

Doerks, et al., "Protein annotation: detective work for function prediction." 1998, Trends in Genetics, vol. 14, pp. 248–250.*

Seshagiri Somasekar, et al.: "Baculovirus–based genetic screen for antiapoptotic genes identifies a novel IAP." Journal of Biological Chemistry, vol. 274, No. 51, Dec. 17, 1999, pp. 36769–36773, XP002187191; ISSN: 0021–9258; The American Society for Biochemistry and Molecular Biology, Inc., USA.

Ahmad Manzoor, et al., "Spodoptera frugiperda caspase–1, a novel insect death protease that cleaves the nuclear immunophilin FKBP46, is the target of the baculovirus antiapoptotic protein p35.", Journal of Biological Chemistry, vol. 272, No. 3, 1997, pp. 1421–1424, XP002187192; ISSN: 0021–9258, The American Society for Biochemistry and Molecular Biology, Inc., USA.

Huang Qihong, et al.., "Evolutionary conservation of apoptosis mechanisms: Lepiopteran and baculoviral inhibitor of apoptosis proteins are inhibitors of mammalian caspase–9." Proceedings of the National Academy of Science of the United States, vol. 97, No. 4, Feb. 15, 2000, pp. 1427–1432, XP002187193; Feb. 15, 2000, ISSN: 0027–8424, The American Society for Biochemistry and Molecular Biology, Inc., USA.

* cited by examiner

Primary Examiner—Elizabeth F. McElwain
Assistant Examiner—Cynthia Collins
(74) Attorney, Agent, or Firm—Townsend and Townsend and Crew, LLP

(57) ABSTRACT

The present invention is generally directed to Inhibitor of Apoptosis Proteins ("IAPs"), nucleic acid molecules encoding IAPs, viral vectors, recombinant baculoviruses comprising an IAP, transgenic plants comprising an IAP nucleic acid, and methods of assaying for compounds which bind to an IAP. In general, the IAP nucleic acids of the invention have 95% or higher identity to SEQ ID NO:1 and the IAP of the invention have 90% or higher identity to SEQ ID NO:3.

17 Claims, No Drawings

SEQUENCE LISTING

<160> NUMBER OF SEQ ID NOS: 7

<210> SEQ ID NO 1
<211> LENGTH: 1739
<212> TYPE: DNA
<213> ORGANISM: Spodoptera frugiperda
<220> FEATURE:
<223> OTHER INFORMATION: fall armyworm inhibitor of apoptosis protein
      (SfIAP) nucleotide sequence including 5' and 3'
      untranslated regions, full length SfIAP cDNA
<221> NAME/KEY: CDS
<222> LOCATION: (229)..(1362)
<223> OTHER INFORMATION: fall armyworm inhibitor of apoptosis protein
      (SfIAP)

<400> SEQUENCE: 1

```
agttttagtc cgaacgccga cgagtgacgc atgttacgag cctactgtac tgactcgact     60
cgaaccgcga tcgatcgtgg accgctgtaa acgtcacttc gtttcgttcg ttagtcgcga    120
gtttcgcact catgttggag agttgtgttg tttgtttatc agtccgttaa cgtttgacca    180
gtgagagtga gaacagtttt taaaacctag tcataaacaa tcaatttgat gtggtcgtgt    240
tccttacctt gttggaatac aaaaaaatct ggattacaaa tggatattac caaagtggca    300
tccaatggct cctcctcaac attaacgcta ttcaagagcg gatcgcttga ggctaaaatt    360
cgacctctcg cgccactaat gctgccgacg ccaagttacg actccaacgc cggctctcca    420
tctttgtctc catccacgcc ttgctcttca tcttctttct ccattgataa aaccgacaac    480
cacgacacct tcggcttcag tgcggacaca gttgatatga aaagagga tgaacgtatg      540 aaaacatttg aaaaatggcc cgtaagtttt ctatccggag agcaacttgc tcgaaatgga    600
ttttactacc tcggccgtag agatgaagcc cgttgcgctt tctgtaaagt ggagattatg    660
aggtgggtgg agggcgatga ccctgcgaag gaccatcagc gttgggcgcc acagtgccca    720
tttgtgcgca aattgaacgg tactgcagca gcagacacgg gtagttcggg ccaggacgag    780
tgtggtgccc gcgccgctcc ctccggtacc tctccgccgc gtatggccgg tcccgtgcac    840
ccacgatatg catctgaagc cgcacgacta cgcagtttta aagactggcc acgatgcatg    900
cgacaaaaac ctgaagaact cgccgaggct ggcttttttt acactggtca gggagacaaa    960
accaagtgtt tttattgcga tggtggatta aaagattggg agaaccatga cgtaccctgg   1020
gaacaacacg caaggtggtt tgaccgttgc gcctacgtgc aattggtgaa gggtcgagaa   1080
tacgttcaaa aggtgatttc tgaagcttgt gaggtatccg cgtcagaagc ggaacgtgat   1140
gtagcacccg cacggactgc cgagccaagc ccgccagcag aggcgccaga aaactcagtc   1200
gatgactcaa agttgtgtaa aatctgttat gctgaagagc gtaacgtgtg cttcgtgccg   1260
tgcggccacg tggtggcttg cgccaagtgc gcgctggcgg ccgacaagtg ccccatgtgc   1320
cgcaggacgt ttcaaaatgc agtgcggtta tatttctcgt gagaagagcc accaatttgc   1380
aggctcaatt ctagtcttaa gggacgaccg gacagagctg tgtgctgaaa ccatgagctc   1440
gtatgtcacg tttccacagg cggagaaacc tattaaaact tattgtttga tggtttcgat   1500
aggaactcgc tcgctagtgt agcaaaagac gaaattgaaa ggttcctcag gagtaagaca   1560
gatatactta gttatagtga attataaaat acatagcata cattaagatt atatattgat   1620
gacgcttatt actttaattc acgttccaat ttgacgtgtt attacaatta tttatttttac  1680 acagatgtaa cgaaaacttt gtgtgagatg taacatttac accgaaaaaa aaaaaaaaa    1739
```

```
<210> SEQ ID NO 2
<211> LENGTH: 1134
<212> TYPE: DNA
<213> ORGANISM: Spodoptera frugiperda
<220> FEATURE:
<223> OTHER INFORMATION: SfIAP nucleotide sequence, open reading frame
      (ORF) only
<221> NAME/KEY: CDS
<222> LOCATION: (1)..(1134)
<223> OTHER INFORMATION: fall armyworm inhibitor of apoptosis protein
      (SfIAP)

<400> SEQUENCE: 2 atg tgg tcg tgt tcc tta cct tgt tgg aat aca aaa aaa tct gga tta         48
Met Trp Ser Cys Ser Leu Pro Cys Trp Asn Thr Lys Lys Ser Gly Leu
 1               5                  10                  15 caa atg gat att acc aaa gtg gca tcc aat ggc tcc tcc tca aca tta         96
Gln Met Asp Ile Thr Lys Val Ala Ser Asn Gly Ser Ser Ser Thr Leu
             20                  25                  30 acg cta ttc aag agc gga tcg ctt gag gct aaa att cga cct ctc gcg        144
Thr Leu Phe Lys Ser Gly Ser Leu Glu Ala Lys Ile Arg Pro Leu Ala
         35                  40                  45 cca cta atg ctg ccg acg cca agt tac gac tcc aac gcc ggc tct cca        192
Pro Leu Met Leu Pro Thr Pro Ser Tyr Asp Ser Asn Ala Gly Ser Pro
     50                  55                  60 tct ttg tct cca tcc acg cct tgc tct tca tct tct ttc tcc att gat        240
Ser Leu Ser Pro Ser Thr Pro Cys Ser Ser Ser Ser Phe Ser Ile Asp
 65                  70                  75                  80 aaa acc gac aac cac gac acc ttc ggc ttc agt gcg gac aca gtt gat        288
Lys Thr Asp Asn His Asp Thr Phe Gly Phe Ser Ala Asp Thr Val Asp
                 85                  90                  95 atg aga aaa gag gat gaa cgt atg aaa aca ttt gaa aaa tgg ccc gta        336
Met Arg Lys Glu Asp Glu Arg Met Lys Thr Phe Glu Lys Trp Pro Val
            100                 105                 110 agt ttt cta tcc gga gag caa ctt gct cga aat gga ttt tac tac ctc        384
Ser Phe Leu Ser Gly Glu Gln Leu Ala Arg Asn Gly Phe Tyr Tyr Leu
        115                 120                 125 ggc cgt aga gat gaa gcc cgt tgc gct ttc tgt aaa gtg gag att atg        432
Gly Arg Arg Asp Glu Ala Arg Cys Ala Phe Cys Lys Val Glu Ile Met
    130                 135                 140 agg tgg gtg gag ggc gat gac cct gcg aag gac cat cag cgt tgg gcg        480
Arg Trp Val Glu Gly Asp Asp Pro Ala Lys Asp His Gln Arg Trp Ala
145                 150                 155                 160 cca cag tgc cca ttt gtg cgc aaa ttg aac ggt act gca gca gca gac        528
Pro Gln Cys Pro Phe Val Arg Lys Leu Asn Gly Thr Ala Ala Ala Asp
                165                 170                 175 acg ggt agt tcg ggc cag gac gag tgt ggt gcc cgc gcc gct ccc tcc        576
Thr Gly Ser Ser Gly Gln Asp Glu Cys Gly Ala Arg Ala Ala Pro Ser
            180                 185                 190 ggt acc tct ccg ccg cgt atg gcc ggt ccc gtg cac cca cga tat gca        624
Gly Thr Ser Pro Pro Arg Met Ala Gly Pro Val His Pro Arg Tyr Ala
        195                 200                 205 tct gaa gcc gca cga cta cgc agt ttt aaa gac tgg cca cga tgc atg        672
Ser Glu Ala Ala Arg Leu Arg Ser Phe Lys Asp Trp Pro Arg Cys Met
    210                 215                 220 cga caa aaa cct gaa gaa ctc gcc gag gct ggc ttt ttt tac act ggt        720
Arg Gln Lys Pro Glu Glu Leu Ala Glu Ala Gly Phe Phe Tyr Thr Gly
225                 230                 235                 240 cag gga gac aaa acc aag tgt ttt tat tgc gat ggt gga tta aaa gat        768
Gln Gly Asp Lys Thr Lys Cys Phe Tyr Cys Asp Gly Gly Leu Lys Asp
                245                 250                 255 tgg gag aac cat gac gta ccc tgg gaa caa cac gca agg tgg ttt gac        816
Trp Glu Asn His Asp Val Pro Trp Glu Gln His Ala Arg Trp Phe Asp
```

```
                Trp Glu Asn His Asp Val Pro Trp Glu Gln His Ala Arg Trp Phe Asp
                            260                 265                 270 cgt tgc gcc tac gtg caa ttg gtg aag ggt cga gaa tac gtt caa aag              864
Arg Cys Ala Tyr Val Gln Leu Val Lys Gly Arg Glu Tyr Val Gln Lys
            275                 280                 285 gtg att tct gaa gct tgt gag gta tcc gcg tca gaa gcg gaa cgt gat              912
Val Ile Ser Glu Ala Cys Glu Val Ser Ala Ser Glu Ala Glu Arg Asp
        290                 295                 300 gta gca ccc gca cgg act gcc gag cca agc ccg cca gca gag gcg cca              960
Val Ala Pro Ala Arg Thr Ala Glu Pro Ser Pro Pro Ala Glu Ala Pro
305                 310                 315                 320 gaa aac tca gtc gat gac tca aag ttg tgt aaa atc tgt tat gct gaa             1008
Glu Asn Ser Val Asp Asp Ser Lys Leu Cys Lys Ile Cys Tyr Ala Glu
                325                 330                 335 gag cgt aac gtg tgc ttc gtg ccg tgc ggc cac gtg gtg gct tgc gcc             1056
Glu Arg Asn Val Cys Phe Val Pro Cys Gly His Val Val Ala Cys Ala
            340                 345                 350 aag tgc gcg ctg gcg gcc gac aag tgc ccc atg tgc cgc agg acg ttt             1104
Lys Cys Ala Leu Ala Ala Asp Lys Cys Pro Met Cys Arg Arg Thr Phe
        355                 360                 365 caa aat gca gtg cgg tta tat ttc tcg tga                                     1134
Gln Asn Ala Val Arg Leu Tyr Phe Ser
    370                 375

<210> SEQ ID NO 3
<211> LENGTH: 377
<212> TYPE: PRT
<213> ORGANISM: Spodoptera frugiperda
<220> FEATURE:
<223> OTHER INFORMATION: fall armyworm inhibitor of apoptosis protein
      (SfIAP)

<400> SEQUENCE: 3

Met Trp Ser Cys Ser Leu Pro Cys Trp Asn Thr Lys Lys Ser Gly Leu
  1               5                  10                  15

Gln Met Asp Ile Thr Lys Val Ala Ser Asn Gly Ser Ser Ser Thr Leu
                20                  25                  30

Thr Leu Phe Lys Ser Gly Ser Leu Glu Ala Lys Ile Arg Pro Leu Ala
            35                  40                  45

Pro Leu Met Leu Pro Thr Pro Ser Tyr Asp Ser Asn Ala Gly Ser Pro
        50                  55                  60

Ser Leu Ser Pro Ser Thr Pro Cys Ser Ser Ser Phe Ser Ile Asp
 65                  70                  75                  80

Lys Thr Asp Asn His Asp Thr Phe Gly Phe Ser Ala Asp Thr Val Asp
                85                  90                  95

Met Arg Lys Glu Asp Glu Arg Met Lys Thr Phe Glu Lys Trp Pro Val
                100                 105                 110

Ser Phe Leu Ser Gly Glu Gln Leu Ala Arg Asn Gly Phe Tyr Tyr Leu
            115                 120                 125

Gly Arg Arg Asp Glu Ala Arg Cys Ala Phe Cys Lys Val Glu Ile Met
        130                 135                 140

Arg Trp Val Glu Gly Asp Asp Pro Ala Lys Asp His Gln Arg Trp Ala
145                 150                 155                 160

Pro Gln Cys Pro Phe Val Arg Lys Leu Asn Gly Thr Ala Ala Ala Asp
                165                 170                 175

Thr Gly Ser Ser Gly Gln Asp Glu Cys Gly Ala Arg Ala Ala Pro Ser
            180                 185                 190

Gly Thr Ser Pro Pro Arg Met Ala Gly Pro Val His Pro Arg Tyr Ala
```

195                 200                 205
Ser Glu Ala Ala Arg Leu Arg Ser Phe Lys Asp Trp Pro Arg Cys Met
    210                 215                 220

Arg Gln Lys Pro Glu Glu Leu Ala Glu Ala Gly Phe Phe Tyr Thr Gly
225                 230                 235                 240

Gln Gly Asp Lys Thr Lys Cys Phe Tyr Cys Asp Gly Gly Leu Lys Asp
                245                 250                 255

Trp Glu Asn His Asp Val Pro Trp Glu Gln His Ala Arg Trp Phe Asp
                260                 265                 270

Arg Cys Ala Tyr Val Gln Leu Val Lys Gly Arg Glu Tyr Val Gln Lys
                275                 280                 285

Val Ile Ser Glu Ala Cys Glu Val Ser Ala Ser Glu Ala Glu Arg Asp
    290                 295                 300

Val Ala Pro Ala Arg Thr Ala Glu Pro Ser Pro Pro Ala Glu Ala Pro
305                 310                 315                 320

Glu Asn Ser Val Asp Asp Ser Lys Leu Cys Lys Ile Cys Tyr Ala Glu
                325                 330                 335

Glu Arg Asn Val Cys Phe Val Pro Cys Gly His Val Val Ala Cys Ala
                340                 345                 350

Lys Cys Ala Leu Ala Ala Asp Lys Cys Pro Met Cys Arg Arg Thr Phe
                355                 360                 365

Gln Asn Ala Val Arg Leu Tyr Phe Ser
    370                 375

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:degenerate
      primer
<221> NAME/KEY: modified_base
<222> LOCATION: (1)..(20)
<223> OTHER INFORMATION: n = a, c, g or t

<400> SEQUENCE: 4
gcngangcng gnttyttyta                                                    20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:degenerate
      primer
<221> NAME/KEY: modified_base
<222> LOCATION: (1)..(17)
<223> OTHER INFORMATION: n = a, c, g or t

<400> SEQUENCE: 5
acnacrtgnc crcangg                                                       17

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:internal PCR
      primer

<400> SEQUENCE: 6
cacttggttt tgtctccctg acc                                                23

```
<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:internal PCR
      primer

<400> SEQUENCE: 7
actcaaagtt gtgtaaaatc tg                                             22
```

NUCLEIC ACIDS ENCODING PLANT INHIBITORS OF APOPTOSIS AND TRANSGENIC CELLS AND PLANTS EXPRESSING THEM

STATEMENT AS TO RIGHTS TO INVENTIONS MADE UNDER FEDERALLY SPONSORED RESEARCH AND DEVELOPMENT

This invention was made with government support under RO1 ES 02710 awarded by the National Institute of Environmental Health Sciences and under 97 35302 4406 awarded by the United States Department of Agriculture. The government has certain rights in the invention.

CROSS-REFERENCE TO RELATED APPLICATIONS

Not applicable.

FIELD OF THE INVENTION

The present invention is directed to polynucleotides encoding inhibitors of apoptosis. The polynucleotides can be used to control apoptosis in target cells.

BACKGROUND OF THE INVENTION

Apoptosis denotes a type of programmed cell death in which the cell nucleus shrinks, the genetic material (DNA) progressively degrades, and the cell collapses (see, e.g. Kawabe, et al. *Nature* 349:245–248 (1991). In many organisms, apoptosis plays an important physiological role in development, tissue homeostasis, eradication of virus-infected cells, and other events (Wyllie, A. H., Kerr, J. F. R. & Currie, A. R. (1980) *Int. Rev. Cytol.* 68, 251–306)). Caspases are a family of intracellular proteases responsible for execution of the apoptotic program (Salvesen, G. S. & Dixit, V. M. (1997) *Cell* 91, 443–446). They are initially synthesized as inactive zymogens that are activated by proteolytic processing, generating the requisite large- and small-subunits which comprise the active caspase enzyme. The functional conservation of caspases in inducing apoptosis within various insect, plant, and animal species makes them appropriate targets for influencing the apoptosis process.

Some viruses harbor genes which encode caspase inhibitory proteins, thereby suppressing host defense mechanisms which would otherwise eliminate virus-infected cells by apoptosis. Examples of viral caspase inhibitors include the baculoviral p35 protein (Clem, R. J. et al., (1991) *Science* 254, 1388–1390 and the crmA protein of the Poxviridae-family cowpox virus (Ray, C., et al., (1992) *Cell* 69, 597–604). IAP family proteins were first discovered in baculoviruses (Birnbaum, M., et al., (1994) *Journal of Virology* 68:2521–2525; Crook, N. E., et al., (1993) *J. Virol.* 67: 2168–2174). Genetic complementation analysis revealed that the Inhibitor of Apoptosis Protein ("IAP") genes of the CpGV and OpMNPV baculoviruses can rescue p35-deficient viruses, maintaining host cell survival so that viral replication successfully occurs (Birnbaum, M., (1994), supra, Crook, N. E., et al., (1993) supra). Baculoviral IAPs contain two tandem copies of a Baculovirus Inhibitory Repeat (BIR) domain followed by a C-terminal RING domain. Mutagenesis studies suggest a requirement for both the BIR and RING domains for their anti-apoptotic function in insect cells. Since these initial discoveries, cellular IAP homologs have been found in many animal species, including Drosophila, mammals, and humans (reviewed in (Miller, L. (1999) *Trends in Cell Biology* 9:323–328; Deveraux, Q. & Reed, J. C. (1998) *Genes Dev.* 13:239–252)). All cellular IAPs contain one to three copies of a baculoviral inhibitory repeat (BIR) domain and most also contain a RING domain located near their C-termini. A mechanism for IAP-family proteins was shown when it was reported that several human IAPs, including XIAP, cIAP1, cIAP2, can directly bind and inhibit certain caspases, including caspases-3, -7, and -9 (Deveraux, Q., et al., (1999) *EMBO J., in press.; Deveraux, Q. & Reed, J. C.* (1998) supra; Deveraux, Q., et al. (1997) *Nature* 388:300–303; Roy, N., et al., (1997) *EMBO J.* 16, 6914–6925). Subsequent deletional analysis indicated that the second BIR domain (BIR2) of XIAP is sufficient for inhibiting mammalian caspases-3 and -7 (Roy, N., et al., (1997), supra; Takahashi, R. et al., (1998) *J. Biol. Chem.* 273, 7787–7790). However, recently it was shown that a fragment of XIAP encompassing the third BIR domain (BIR3) and RING domain specifically inhibits mammalian caspase-9 (Takahashi, R. et al., (1998), supra). Thus, among mammalian IAPs, different regions of these proteins appear to mediate inhibitory interactions with specific caspases.

Though other types of mechanisms have not been excluded, it has been suggested that Drosophila and baculovirus IAPs also may inhibit some caspases. It has been shown that Drosophila IAP1 (DIAP1) is able to inhibit drICE and DCP-1 in insect cells and in yeast (Kaiser, W. et al., (1998) *FEBS Lett.* 440, 243–248; Hawkins, C., et al., (1999) *Proc. Natl. Acad. Sci. USA* 96, 2885–2890). It has also been shown that CpIAP and OpIAP require both BIR and RING domains to inhibit activation of Sf-caspase-1 during baculovirus-induced apoptosis in Sf-21 cells. (Seshagiri, S. & Miller, L. K. (1997) *Proc. Natl. Acad. Sci. USA* 94, 13606–13611.)

Interestingly, a group of apoptosis-inducing genes which encode IAP-binding proteins has been identified in Drosophila, including reaper, hid, and grim (White, E. & Cipriani, R. (1989) *Proc. Natl. Acad. Sci. USA* 86, 9886–9890). The Reaper, Hid, and Grim proteins contain a homologous 14 amino acid N-terminal domain which is both necessary and sufficient for binding DIAP 1 and for inducing apoptosis (Vucic, D., et al., (1997) *Proc. Natl. Acad. Sci. USA* 94, 10183–10188; Vucic, D., et al., (1998) *Mol. Cell. Biol.* 18, 3300–3309). Though initially controversial (reviewed in Deveraux, Q. & Reed, J. C. (1998) *Genes Dev.* 13, 239–252; Miller, L. (1999) *Trends in Cell Biology* 9, 323–328), recent data suggest that Reaper, Hid, and Grim induce apoptosis by inhibiting IAPs thus interfering with IAP-mediated suppression of caspases (Wang, S., et al., (1999) *Cell* 98, 453–463).

SUMMARY OF THE INVENTION

The invention provides a cDNA for an Inhibitor of Apoptosis Protein ("IAP") from *Spodoptera frugiperda* (fall armyworm) (SEQ ID NO:1), as well as nucleic acids that are 85% or more identical to that cDNA. Further, the invention provides polypeptides that are at least 90% identical to a polypeptide encoded by SEQ ID NO:1 (the polypeptide is SEQ ID NO:3). In preferred embodiments, the polypeptides are at least 95% identical to SEQ ID NO:3.

The invention further provides host cells comprising recombinant expression cassettes comprising a promoter operably linked to a polynucleotide at least 85% identical to SEQ ID NO:1, at least 95% identical to SEQ ID NO:1, or that comprises SEQ ID NO:1. The promoter can be inducible or can be constitutive. The host cell can be an insect cell, a plant cell, a mammalian cell. The invention provides recombinant expression cassettes comprising polynucleotides that are 85% or more identical to, 95% or more identical to, or that comprises SEQ ID NO:1. The recombinant expression cassette will typically comprise a promoter, which promoter can be inducible or can be constitutive.

The invention further provides recombinant baculoviruses which have been engineered to contain a nucleic acid which is 85% or more identical to SEQ ID NO:1, which is 95% or more identical to SEQ ID NO:1, or which comprises SEQ ID NO:1. The invention further provides transgenic plants which contain a nucleic acid which is 85% or more identical to SEQ ID NO:1, which is 95% or more identical to SEQ ID NO:1, or which comprises SEQ ID NO:1.

The invention further provides in vitro methods of assaying for compounds capable of specifically binding to an IAP, wherein the method comprises combining an IAP with a test compound and assaying whether the test compound specifically binds to the IAP, where the IAP has a sequence at least 90% or more identical to SEQ ID NO:3. In preferred embodiments, the LAP has a sequence at least 95% identical to SEQ ID NO:3. The IAP can be immobilized on a solid support or can be in an aqueous solution. In some embodiments, the test compound can be bound to a solid support and contacted with the IAP.

The invention further provides in vitro methods of assaying for modulators of IAP activity wherein the method comprises combining an IAP with a test compound and assaying whether the test compound can increase or decrease IAP binding specifically to a capsase polypeptide. The IAP can be immobilized on a solid support or can be in an aqueous solution. In some embodiments, the test compound can be bound to a solid support and contacted with the IAP.

The invention further provides an in vitro method of assaying for the presence of IAP cDNA comprising hybridizing said cDNA to a nucleic acid 85% or more identical to SEQ ID NO:1 or to a contiguous portion of SEQ ID NO:1 at least 20 nucleotides in length and detecting hybridization of the cDNA and the nucleic acid, wherein detection of said hybridization is indicative of the presence of said IAP cDNA. The method further provides an in vitro method of assaying for the presence of an IAP comprising binding the IAP with an antibody which specifically binds said IAP, or with a fragment of said antibody which retains specificity for said IAP, and detecting said binding, wherein said detection is indicative of the presence of the IAP. The detection can be by an ELISA, a Western blot, or other methods known in the art.

DESCRIPTION OF THE SPECIFIC EMBODIMENTS

Introduction

Apoptosis, or programmed cell death, is an essential process for normal development and homeostasis in multicellular organisms. It plays an important role in disease resistance in organisms as diverse as insects, plants and higher animals, including mammals. In insects, for example, resistance to viral infection includes apoptosis of infected cells, thereby limiting the spread of the invading pathogen. Similarly, in plants, apoptosis of infected cells limits the ability of viral and other infections to spread. This tendency of plants to react to infection by apoptosis of infected cells is in fact exploited by some fungi to create lesions exposing plant tissue more susceptible to fungal invasion. In mammals, such as humans, apoptosis kills cells which have undergone damage to their DNA when they go through the G2/M checkpoint. Many cancers are able to grow because they are able to avoid this control mechanism. Thus, the ability to modulate apoptosis (that is, to increase or to decrease it at will) is useful for modulating the ability of plants and of insects and other animals to pathogens and cancer, Spodoptera frugiperda (fall armyworm) is a lepidopteran host of the Autographa Califomica Nuclear Polyhedrosis Virus (AcMNPV), a member of the baculovirus family. Despite extensive use of S. frugiperda-derived cells for studies of apoptosis-regulation by baculoviruses (reviewed in (Miller, L. (1999) Trends in Cell Biology 9, 323–328)), no endogenous apoptosis-regulating genes have yet been identified in these insect cells, with the exception of Sf-caspases-1 (Ahmad, M., Srinivasula, S., Wang, L., Litwack, G., Fernandes-Alnenri, T. & Alnenri, E. (1997) J. Biol. Chem. 272, 1421–1424).

The present invention demonstrates the cloning and chacterizating of a cellular IAP from S. frugiperda (SfIAP). Sf has been deposited with GenBank and will be publicly available after the filing of this specification under accession number AF186378. SfIAP shares considerable sequence similarity with baculoviral IAPs (vIAPs), suggesting these viruses acquired their vIAP genes from host cells. Analysis of the SfIAP and CpIAP proteins indicates that they are direct inhibitors of mammalian caspase-9, suggesting evolutionary conservation of IAP-family protein functions and providing an explanation for previous reports that baculovirus IAPs can inhibit apoptosis induced by many stimuli in mammalian cells (Hawkins, C. J., Uren, A. G., Hacker, G., Medcalf, R. L. & Vaux, D. L. (1996) Proc. Natl. Acad. Sci. USA 93, 13786–13790; Hawkins, C., Ekert, P., Uren, A., Holmgreen, S. & Vaux, D. (1998) Cell Death and Differentiation 5, 569–576; Uren, A. G., Pakusch, M., Hawkins, C. J., Puls, K. L. & Vaux, D. L. (1996) Proc. Natl. Acad. Sci. USA 93, 4974–4978). Other IAPs are available in GenBank under accession numbers U45880 (human),U75285 (human),U45879 (human), U45878 (human), NM 009689 (mouse), NM 009688 (mouse), L05494 (baculovirus), and L224564 (baculovirus).

Peptides corresponding the N-terminal IAP-binding domain of Grim negate the ability of SfIAP and CpIAP to inhibit mammalian caspases in vitro, providing evidence that mechanisms similar to those described in Drosophila may be used to regulate the IAPs of Spodoptera frugiperda and baculoviruses.

The IAPs of the invention provide a convenient new way to screen for compounds which can modulate apoptosis. Additionally, recombinant viruses encoding IAPs of the invention can be used to infect undesirable insects. The IAPs then decrease the ability of the insects to limit the resulting infection, with increased mortality. Further, IAPs of the invention can be used to transfect plants to render the plants less susceptible to fungi and other organisms which exploit the normal apoptosis response of the plant to render it more vulnerable to invasion. Further, the IAPs of the invention can be used in animals to combat various disorders in which apoptosis plays a role. In preferred embodiments, the animal is a mammal. In particularly preferred uses, the mammal is a human.

The invention can be exploited in a variety of ways. Polypeptides of the invention can be directly administered as therapeutic agents. For use in animals, such as humans, the polypeptides can be administered intravenously, or they can be encapsulated and administered orally. Cells can be transfected with antisense oligonucleotides to bind to IAP-encoding nucleic acids and block their expression. Small chemical compounds which block the binding of IAPs to caspases can be used to interfere with the normal activity of LAPs.

The IAPs of the invention can also be used in vitro to monitor for expression of IAP cDNA. Conveniently, this can be done by immobilizing nucleic acid of an IAP of the invention on a solid substrate, such as a "chip," permitting the nucleic acid to act as a probe to screen a cDNA library or cDNA from a sample of interest. Typically, the length of the nucleic acid from the IAP of the invention used as a probe is chosen to be sufficiently long to permit specific hybridization to a cDNA of a IAP of the invention as opposed to other IAPs. Conveniently, such probes are 20 nucleotides or more, or 25, 30, 35, 40, 45, 50, or even more in length, to permit specific detection of the target cDNAs.

In another set of embodiments, the IAPs of the invention can be used to detect and monitor the presence of IAPs in a sample. Typically, antibodies are generated against an IAP of the invention. Depending on the purpose of the assays, the antibodies can be such that they detect all IAPs, or the antibodies can be absorbed against other known IAPs to eliminate antibodies which recognize IAPs other than those of the invention. Methods of generating antibodies against antigens are well known in the art. Typically, monoclonal antibodies are preferred. Fragments of antibodies which retain binding specificity for the IAP can also be used. Fragments such as single chain Fvs (scFvs), disufide stabilized Fvs (dsFvs), Fabs, and Fab's are well known in the art. Assays employing such antibodies, such as ELISAs and Western blots, are also well known in the art.

Definitions

"IAP" refers generally to an inhibitor of apoptosis protein and, more specifically herein, to an inhibitor of apoptosis protein of the invention. Which use is intended will be clear in context. IAPs of the invention typically are at least substantially identical to SEQ ID NO:3. "SfIAP" specifically denotes an IAP of the invention cloned from *Spodoptera frugiperda* (fall armyworm). All cellular IAPs contain one to three copies of a baculoviral inhibitory repeat (BIR) domain and most also contain a RING domain located near their C-termini. SfIAP contains two BIR domains, followed by a RING domain near its C-terminus. Within the BIR and RING regions, SfIAP shares 85% amino acid identity (90% similarity) with baculoviral CpIAP and 70% identity (80% similarity) with OpIAP.

"Apoptosis" refers to programmed cell death. It is an essential process for normal development and homeostasis in multicellular organisms such as mammals, insects and plants. Apoptosis differs from general cell death as from a toxin or ischemic event in that the cell is shutting down according to a controlled pattern of events.

"Apoptosis-inducing chemical" refers to a chemical that promotes programmed cell death. The chemical can be administered directly to the plant or indirectly by secretion of a pathogen.

"Heterologous gene" refers to a gene introduced into a host cell via recombinant technology where that gene is either not naturally present in the cell or represents an additional copy of an endogenous gene or is operably linked to a promoter that is not normally found in association with the gene in the host cell.

"Inducible plant promoter" refers to a promoter which directs expression of a gene where the level of expression is alterable by factors such as temperature, pH, transcription factors and chemicals.

"Insecticidal protein" refers to a diverse group of compounds that are lethal to insects when ingested. Examples include the crystal proteins or delta endotoxins from *Bacillus thuringiensis*.

"Viral plant disease resistance" refers to the ability of a plant to prevent or inhibit a viral pathogen from successfully infecting it.

"Operably linked" refers to nucleotide sequences which are joined in such a manner that their individual function complements each other. Examples are promoters, transcription terminators, enhancers or activators and heterologous genes which when transcribed and if appropriate to translate will produce a functional product, i.e. a protein, ribozyme or anti-sense construct.

"Plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

"Plant pathogens" refer to fungi, bacteria, virus and insects that infect plants and have negative effects on their growth and health.

"Promoter" refers to a region of DNA involved in binding the RNA polymerase to initiate transcription.

"Transformation rate" refers to the percent of cells that are successfully incorporate a heterologous gene into its genome and survive.

"Transfecting" refers to the process of introducing a heterologous gene into a cell.

The term "protein" is used herein interchangeably with "polypeptide" and "peptide."

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, hosphorothioates, phosphoramidates, methyl phosphonates, chiral-methyl hosphonates, 2-O-methyl ribonucleotides, peptide-nucleic acids (PNAs).

Unless otherwise indicated, a particular nucleic acid sequence also implicitly encompasses conservatively modified variants thereof(e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) *J. Biol. Chem.* 260:2605–2608; Rossolini et al. (1994) *Mol. Cell. Probes* 8:91–98). The term nucleic acid is used interchangeably with gene, cDNA, mRNA, oligonucleotide, and polynucleotide.

A polynucleotide sequence comprising a fusion protein of the invention hybridizes under stringent conditions to each of the nucleotide sequences encoding each individual polypeptide of the fusion protein. The polynucleotide sequences encoding the individual polypeptides of the fusion polypeptide therefore include conservatively modified variants, polymorphic variants, alleles, mutants, subsequences, and interspecies homologs.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 85% sequence identity. Alternatively, percent identity can be any integer from 85% to 100%. More preferred embodiments include at least: 85%, 90%, 95%, or 99% or higher, compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. "Substantial identity" of amino acid sequences for these purposes normally means sequence identity of at least 87%. Preferred percent identity of polypeptides can be any integer from 87% to 100%. More preferred embodiments include at least 87%, 90%, 95%, or 99% identity. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Optimal alignment of sequences for comparison may be conducted by the local identity algorithm of Smith and Waterman (1981) *Add. APL. Math.* 2:482, by the identity alignment algorithm of Needleman and Wunsch (1970) *J. Mol. Biol.* 48:443, by the search for similarity method of Pearson and Lipman (1988) *Proc. Natl. Acad. Sci. (U.S.A.)* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

A preferred example of algorithms that are suitable for determining percent sequence identity and sequence similarity are the BLAST and BLAST 2.0 algorithms, which are described in Altschul et al. (1977) *Nuc. Acids Res.* 25:3389–3402 and Altschul et al. (1990) *J. Mol. Biol.* 215:403–410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

Another indication that nucleotide sequences are substantially identical is if two molecules hybridize to each other, or to a third nucleic acid, under moderately, and preferably highly, stringent conditions. Stringent conditions are sequence dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993) (Elsevier Science, Inc., New York). Generally, stringent conditions are selected to be about 5–10° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

For the purpose of the invention, suitable "moderately stringent conditions" include, for example, prewashing in a solution of 5×SSC, 0.5% SDS, 1.0 mM EDTA (pH 8.0), hybridizing at 50° C.–65° C., 5× SSC overnight, followed by washing twice at 65° C. for 20 minutes with each of 233 , 0.5× and 0.2× SSC (containing 0.1% SDS). Such hybridizing DNA sequences are also within the scope of this invention.

Screening for IAP Binding Activity

The invention provides in vitro and in vivo methods of assaying for a modulator of IAP activity by identifying molecules that specifically bind an IAP, thereby affecting its activity. While the invention is not limited by what means the IAP activity is inhibited, specific embodiments include assaying for IAP binding to members of the caspase family, as described herein. The methods of the invention also include screening for antibodies directed to an IAP or small molecule binders of IAPs. To assay for specific binding of a putative modulatory molecule, the IAP can be in solution or can be attached to a fixed substrate. In some embodiments, an IAP is fixed to a solid substrate for high throughput screenings or column chromatography.

High-Throughput Screening of Candidate Agents that Bind IAPs of the invention

Conventionally, new chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery. Because of the ability to test large numbers quickly and efficiently, high throughput screening (HTS) methods are replacing conventional lead compound identification methods.

In one embodiment, high throughput screening methods are used to identify compositions that specifically bind an IAP and modulate its activity. This involves providing a library containing a large number of potential compounds (candidate compounds). Such "combinatorial chemical libraries" are then screened in one or more assays to identify those library members (particular chemical species or subclasses) that bind IAP. The compounds thus identified can serve as conventional "lead compounds" or can themselves be used as potential or actual reagents.

Combinatorial chemical libraries

A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks can result in the theoretical synthesis of 100 million tetrameric compounds or 10 billion pentameric compounds (see, e.g., Gallop (1994) 37:1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37:487–493, Houghton (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs (1993) *Proc. Nat. Acad. Sci. USA* 90: 6909–6913), vinylogous polypeptides (Hagihara (1992) *J. Amer. Chem. Soc.* 114: 6568), nonpeptidal peptidomimetics with a Beta-D-Glucose scaffolding (Hirschmann (1992) *J. Amer. Chem. Soc.* 114: 9217–9218), analogous organic syntheses of small compound libraries (Chen (1994) *J. Amer. Chem. Soc.* 116: 2661), oligocarbamates (Cho (1993) *Science* 261:1303), and/or peptidyl phosphonates (Campbell (1994) *J. Org. Chem.* 59: 658). See, generally, Gordon (1994) *J. Med. Chem.* 37:1385, nucleic acid libraries, peptide nucleic acid libraries (see, e.g., U.S. Pat. No. 5,539,083) antibody libraries (see, e.g., Vaughn (1996) *Nature Biotechnol* 14:309–314), and PCT/US96/10287), carbohydrate libraries (see, e.g., Liang (1996) *Science* 274:1520–1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, orpholino compounds U.S. Pat. Nos. 5,506,337, benzodiazepines 5,288,514).

Devices for the preparation of combinatorial libraries are commercially available; see, e.g., 357 MPS, 390 NPS, Advanced Chem Tech, Louisville Ky.; Symphony, Rainin, Woburn, Mass.; 433A Applied Biosystems, Foster City, Calif.; 9050 Plus, Millipore, Bedford, Mass.; the Ultra-high Throughput Screening System (UHTSS™) capable of screening over 100,000 compounds per day, Aurora BioSciences, San Diego, Calif.

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.).

High throughput assays of chemical libraries

Any of the assays for compounds capable of binding IAPs and/or modulating IAP activity described herein are amenable to high throughput screening. These systems (examples of which are described above) can automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

Attaching of the IAP to a Solid Support

IAP, whether full length, or subsequences thereof (e.g., a BIR domain or RING domain) can be bound to a variety of solid supports. Solid supports that can be used in the methods of the invention include polymer beads, membranes (e.g., nitrocellulose or nylon), microtiter dishes (e.g., PVC or polystyrene), test tubes, dip sticks (e.g., glass, PVC, polypropylene, and the like), microfuge tubes, glass, silica, plastic, metallic beads, or substrates such as paper.

Adhesion of a IAP "target" molecule to the solid support can be direct (i.e. directly contacting the solid support) or indirect (a particular compound or compounds are bound to the support and IAP binds to this compound rather than the solid support). Immobilization of compounds can be covalent, e.g., utilizing single reactive thiol groups of cysteine residues (see, e.g., Colliuod (1993) *Bioconjugate Chem.* 4:528–536). Alternatively, compounds can be immobilized non-covalently but specifically, e.g., via immobilized antibodies (see above), as described by Schuhmann (1991) *Adv. Mater.* 3:388–391; Lu (1995) *Anal. Chem.* 67:83–87; or, the biotin/strepavidin system, see, e.g., Iwane (1997) *Biophys. Biochem. Res. Comm.* 230:76–80); or metal chelating, e.g., Langmuir-Blodgett films (Ng (1995) *Lang-* muir 11:4048–4055; Schmitt (1996) *Angew. Chem. Int. Ed. Engl.* 35:317–20; Frey (1996) *Proc. Natl. Acad. Sci. USA* 93:4937–41; Kubalek (1994) *J. Struct. Biol.* 113:117–123; or, metal-chelating self-assembled monolayers, see, e.g., Sigal (1996) *Anal. Chem.* 68:490–497, for binding of polyhistidine fusion proteins.

Indirect binding of IAP can be achieved using a variety of linkers, many of which are commercially available. The reactive ends can be any of a variety of functionalities, e.g., amino reacting ends such as N-hydroxysuccinimide (NHS) active esters, aldehydes, epoxides, isocyanate, and nitroaryl halides; and thiol reacting ends such as pyridyl disulfides, maleimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the crosslinking of sulfhydryl-containing compounds. The spacer can be aliphatic or aromatic. Examples of commercially available homobifunctional cross-linking reagents include, but are not limited to, the imidoesters such as dimethyl adipimidate dihydrochloride (DMA), dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl (4-iodoacetyl)aminobenzoate (sulfo-SIAB) (Pierce Chemicals, Rockford, Ill.). Another group of coupling agents is the heterobifunctional and thiol cleavable agents such as N-succinimidyl 3-(2-pyridyidithio)propionate (SPDP) (Pierce).

By manipulating the solid support and the mode of attachment of the target IAP molecule to the support, it is possible to control the orientation of the IAP. Thus, for example, it is possible to attach the IAP molecule to a surface in a manner that leaves a "tail" free to interact with other molecules, e.g., a IAP fusion protein with a non-IAP tag e.g., FLAG, myc, GST, polyHis, etc.) for attachment to the column.

Once bound there are a variety of assay formats that can be used to screen for modulators of the IAP. For example, molecules that interact with a IAP binding domain can be identified by attaching the IAP to a solid support, contacting a second molecule with the support coated with IAP, and detecting the binding of the second molecule to the IAP. Molecules that interact or bind with the target are then eluted, thereby isolating molecules that interacted with the IAP.

Assays

A variety of different assays for detecting compounds and compositions capable of binding IAP can be used in this invention. For a general description of different formats for binding assays, see BASIC AND CLINICAL IMMUNOLOGY, 7th Ed. (D. Stiles and A. Terr, ed.)(1991); ENZYME IMMUNOASSAY, E. T. Maggio, ed., CRC Press, Boca Raton, Fla. (1980); and "Practice and Theory of Enzyme Immunoassays" in P. Tijssen, LABORATORY TECHNIQUES IN BIOCHEMISTRY AND MOLECULAR BIOLOGY, Elsevier Science Publishers, B.V. Amsterdam (1985).

In competitive binding assays, the test compound competes with a second compound (known to specifically bind IAP) for specific binding sites on the IAP molecule attached to the solid support. Binding is determined by assessing the amount of second compound associated with the fixed IAP molecule. The amount of second compound associated with IAP is inversely proportional to the ability of a test compound to compete in the binding assay.

The amount of inhibition or stimulation of binding of a labeled second compound by the test compound depends on the binding assay conditions and on the concentrations of labeled analyte and test compounds used. Under specified assay conditions, a test compound is said to be capable of inhibiting the binding of a second compound to a IAP target compound if the amount of bound second compound is decreased by 50% or more compared to a control (no test compound) sample.

Alternatively, various known or unknown compounds, including proteins, carbohydrates, and the like, can be assayed for their ability to directly, and specifically, bind to the target immobilized IAP. In one embodiment, samples from various tissues are contacted with IAP. In another embodiment, small molecule libraries and high throughput screening methods are used to identify compounds that bind to the target. The IAP-binding molecules is then eluted using any method, e.g., column chromatography techniques.

Isolation of nucleic acids of the invention

The nucleic acids of the invention can be used to prepare recombinant proteins and transgenic organisms for a number of purposes. Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989) or Current Protocols in Molecular Biology Volumes 1–3, John Wiley & Sons, Inc. (1994–1998).

The isolation of nucleic acids may be accomplished by a number of techniques. For instance, oligonucleotide probes based on the sequences disclosed here can be used to identify the desired gene in a genomic DNA library. To construct genomic libraries, large segments of genomic DNA are generated by random fragmentation, e.g. using restriction endonucleases, and are ligated with vector DNA to form concatemers that can be packaged into the appropriate vector.

The genomic library can then be screened using a probe based upon the sequence of a cloned IAP gene disclosed here. Probes may be used to hybridize with genomic DNA sequences to isolate homologous genes in the same or different species. Alternatively, antibodies raised against a polypeptide such as an IAD of the invention can be used to screen an expression library. Making antibodies against an antigen of choice is well known in the art.

Alternatively, the nucleic acids of interest can be amplified from nucleic acid samples using amplification techniques. For instance, polymerase chain reaction (PCR) technology can be used to amplify the sequences of IAP genes directly from genomic DNA or from cDNA libraries. PCR and other in vitro amplification methods may also be useful, for example, to clone nucleic acid sequences that code for proteins to be expressed, to make nucleic acids to use as probes for detecting the presence of the desired RNA in samples, for nucleic acid sequencing, or for other purposes. For a general overview of PCR see *PCR Protocols: A Guide to Methods and Applications.* (Innis, M, Gelfand, D., Sninsky, J. and White, T., eds.), *Academic Press*, San Diego (1990). Appropriate primers and probes for identifying sequences from tissues are generated from comparisons of the sequences provided here (e.g. SEQ ID NO: 1, etc.).

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.
Expression in prokaryotes and eukaryotes To obtain high level expression of a cloned gene, such as apolynucleotides encoding IAPs of the invention, one typically subclones polynucleotides encoding the IAP into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the IAP are available in, e.g., *E. coli,* Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains transcription unit or expression cassette that contains all the additional elements required for the expression of the IAP encoding nucleic acid in host cells. A typical expression cassette thus contains a promoter operably linked to the nucleic acid sequence encoding IAP and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to apromoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a IAP encoding sequence under the direction of the polyhedrin promoter or other strong baculovirus promoters.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of the IAP, which are then purified using standard techniques (see, e.g., Colley et al., *J. Biol. Chem.* 264:17619–17622 (1989); *Guide to Protein Purification,* in *Methods in Enzymology,* vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing IAP.

After the expression vector is introduced into the cells, the transfected cells are cultured under conditions favoring expression of IAP, which is recovered from the culture using standard techniques. A number of procedures can be employed when recombinant polypeptides are being purified. For example, proteins having established molecular adhesion properties can be reversible fused to the polypeptides. With the appropriate ligand, the polypeptides can be selectively adsorbed to a purification column and then freed from the column in a relatively pure form. The fused protein is then removed by enzymatic activity. Finally the polypeptides could be purified using immunoaffinity columns.
Production of transgenic plants The IAPs of the invention can be used for increasing plant disease resistance. More specifically, IAPs can be used to delay, suppress or inhibit an apoptosis response in plants. Many plant pathogens, in particular, non-viral plant pathogens, induce apoptosis in plants as a part of the infection process. When a plant is transformed with IAP of the invention, the plant will not be as susceptible to pathogen induced apoptosis and a resistance phenotype is generated.

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. (1984) *EMBO J.* 3:2717–2722. Electroporation techniques are described in Fromm et al. (1985) *Proc. Natl. Acad. Sci. USA* 82:5824. Ballistic transformation techniques are described in Klein et al. (1987) *Nature* 327:70–73.

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants,* Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture,* pp. 124–176, MacMillilan Publishing Company, New York, 1983; and Binding, *Regeneration of Plants, Plant Protoplasts,* pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of IAP mRNA or protein in transgenic plants. Means for detecting and quantitating mRNAs or proteins are well known in the art.

In addition, modulation of apoptosis in plant cells can be monitored. Apoptosis in plants follows an analogous pathway as in animal cells. Two molecular analytic tools are available and established to determine when apoptosis is occurring in plants (as well as animal cells) as distinguished from cell death due to lethal toxins (such as toxic levels of $Fe_2SO_4$) or hypoxic conditions. The first is demonstration of an orderly fragmentation of the cellular DNA. These are called DNA ladders and are readily analyzed using a variety of electrophoretic techniques. The specific gel or running conditions are not critical. Suitable electrophoretic conditions are provided by Wang et al. (1996), *Cell,* 8:375–391.

Alternatively, fragmentation of DNA during apoptosis can be detected in situ by reagents that react with exposed 3'hydroxyl groups on the nucleosomal units. The assay procedure involves end labeling the DNA fragments by terminal deoxynucleotidyl transferase (TdT) with UTP conjugated to a detectable marker. The method is termed (TUNEL) and more details of this method can be found in Wang et al. (supra). Finally one can visually identify apoptotic bodies containing fragmented DNA which is one of the hallmarks of apoptosis.

One of skill can also assay for disease resistance by traditional methods. These methods involve visual observation of the effects of a pathogen on a host plant. Observable symptoms include wilt, rot, stunted growth, color changes and mycelial growth. The symptoms are scored for their degree of intensity in sufficient repeated trials until statistically meaningful information is generated. The generic experimental parameters for reproducible study of infection and resistance in plants is well known.

Preparation of recombinant plant vectors

To use isolated sequences to transform plants, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill. Such genes include for example, ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. XI 5596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of nucleic acid in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. In a preferred embodiment, the promoter is specifically induced by infection of a pathogen. Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in leaves, roots or flowers are useful for enhancing resistance to pathogens that infect those organs. For expression of a IAP in the aerial vegetative organs of a plant, photosynthetic organ-specific promoters, such as the RBCS promoter Khoudi, et al., *Gene* 197:343, 1997), can be used. Root-specific expression of IAP polynucleotides can be achieved under the control of the root-specific ANR1 promoter (Zhang & Forde, *Science,* 279:407, 1998). Any strong, constitutive promoters, such as the CaMV 35S promoter, can be used for the expression of IAP polynucleotides throughout the plant.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Expression in recombinant Baculovirus

Another use of the IAP polynucleotides is in the construction of recombinant baculoviruses that are useful as insecticides. It is known that apoptosis is one of the mechanisms by which insects defend against baculoviral infection. Thus, recombinant baculoviruses comprising the IAP polynucleotides of the invention can be useful in overcoming this defense mechanism.

The construction of most baculovirus expression vector systems has been based on replacement of the polyhedrin gene or other coding region with a foreign gene under the transcriptional control of the polyhedrin gene promoter or other promoter (Pennock, et al., *Mol. and Cell. Bio.* 4:399–406 (1984); and Smith, et al. *Molecular and Cell. Biol.* 3:2156–2165(1983)). Baculoviruses are natural pathogens of many agriculturally important insect pests (Wood, and Granados, *Ann. Rev. Microbiol.* 45:69–87 (1991)). There has thus been an increased interest in exploiting recombinant baculoviruses to express foreign proteins which would improve the pesticidal properties of the native baculoviruse (see, e.g. Carbonell et al., *Gene* 73:409–418 (1988); Hammock, et al., *Nature* 344:458–461 (1990); Maeda, S., *Biochem. Biophys. Res. Comm.* 165: 1177–1183 (1989); Maeda, et al., *Virol.* 184:777–780 (1991) and U.S. Pat. No. 5,908,785).

Administration of IAP Inhibitors, IAPs, and IAP Nucleic Acids and Anti-IAP Nucleic Acids As Pharmaceuticals Apoptosis plays a major role in development, viral pathogenesis, cancer, autoimmune diseases and neurodegenerative disorders. Inappropriate increases in apoptosis may cause or contribute to a variety of diseases, including AIDS, neurodegenerative diseases (e.g. Alzheimer's Disease, Parkinson's Disease, Amyotrophic Lateral Sclerosis (ALS), retinitis pigmentosa and other diseases of the retina, myelodysplastic syndrome (e.g., aplastic anemia), toxin-induced liver disease (e.g., alcoholism) and ischemic injury (e.g., myocardial infarction, stroke, and reperfusion injury). In addition, disruption of normally occurring apoptosis has been implicated in the development of some cancers (e.g. follicular lymphoma, p53 carcinomas, and hormone dependent tumors), autoimmune disorders (e.g., lupus erythematosis and multiple sclerosis) and viral infections (e.g., herpes virus, poxvirus, and adenovirus infections). See, e.g., Korneluk, U.S. Pat. No. 5,919,912.

The invention provides modulators (e.g., inhibitors) of IAP activity and their therapeutic administration. These compounds include those found by the methods of the invention. Modulators that can be used therapeutically also include antibodies and small molecules which bind to IAP to inhibit its ability to bind caspaces. In another embodiment, the modulator is a peptide inhibitor of IAP activity. The peptides, polypeptides and other compositions of the invention are administered with a pharmaceutically acceptable carrier(s) (excipient) to form the pharmacological composition.

Pharmaceutically acceptable carriers and formulations, e.g., for peptides and polypeptides, are known to the skilled artisan and are described in detail in the scientific and patent literature, see e.g., the latest edition of Remington's Pharmaceutical Science, Mack Publishing Company, Easton, Pa. ("Remington's"); Banga; Putney (1998) Nat. Biotechnol. 16:153–157; Patton (1998) Biotechniques 16:141–143; Edwards (1997) Science 276: 1868–1871; Ho, U.S. Pat. No. 5,780,431; Webb, U.S. Pat. No. 5,770,700; Goulmy, U.S. Pat. No. 5,770,201.

The compositions used in the methods of the invention can be delivered alone or as pharmaceutical compositions by any means known in the art, e.g., systemically, regionally, or locally; by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any protocol and in a variety of unit dosage forms depending upon the method of administration, whether it is being co-administered a chemotherapeutic agent, and the like. Dosages for typical peptide and polypeptide pharmaceutical compositions are well known to those of skill in the art. Such dosages are typically advisorial in nature and are adjusted depending on a variety of factors, such as the particular therapeutic context, patient health and the like. The amount of composition or peptide adequate to generate the desired response is defined as a "therapeutically effective dose." The dosage schedule and amounts effective for this use, i.e., the "dosing regimen," will depend upon a variety of factors, including the stage of the disease being treated; timing of co-administration of other agents; the general state of the patient's health; the patient's physical status; age; the pharmaceutical formulation, and the like. The dosage regimen also takes into consideration pharnacokinetics, e.g., the peptide pharmaceutical composition's rate of absorption, bioavailability, metabolism, clearance, and the like, see, e.g., Remington.

Dosages can be determined empirically, e.g, by abatement or amelioration of symptoms, or by objective criteria, analysis of blood or histopathology specimens (amount of apoptosis in a biopsy), and the like.

Vectors used for therapeutic administration of IAP-encoding nucleic acids or anti-IAP nucleic acids, such as antisense molecules, may be viral or nonviral. Viral vectors are usually introduced into a patient as components of a virus. Illustrative viral vectors into which one can incorporate nucleic acids include, for example, adenovirus-based vectors (Cantwell (1996) *Blood* 88:4676–4683; Ohashi (1997) *Proc. Nat'l. Acad. Sci USA* 94:1287–1292), Epstein-Barr virus-based vectors (Mazda (1997) *J. Immunol. Methods* 204:143–151), adenovirus-associated virus vectors, Sindbis virus vectors (Strong (1997) *Gene Ther.* 4: 624–627), herpes simplex virus vectors (Kennedy (1997) *Brain* 120: 1245–1259) and retroviral vectors (Schubert (1997) *Curr. Eye Res.* 16:656–662).

Nonviral vectors encoding products useful in gene therapy can be introduced into an animal by means such as lipofection, biolistics, virosomes, liposomes, immunoliposomes, polycation:nucleic acid conjugates, naked DNA injection, artificial virions, agent-enhanced uptake of DNA, ex vivo transduction. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Naked DNA genetic vaccines are described in, for example, U.S. Pat. No. 5,589,486.

EXAMPLES

The following examples are offered by way of illustration, and are not intended to limit the scope of the present invention or appended claims.

Example 1

Cloning of SfIAP mRNA was isolated from Sf-21 cells using a kit from Qiagen. Degenerate primers were designed according to the consensus amino acid sequences between baculoviral IAPs and Drosophila IAPs, 5'GC(A/C/GT)GA(A/C/G/T)GC(A/C/G/T)GG(AdC/G/T)TT(T/C)T T/C)TA3' (SEQ ID NO:4) and 5'AC(A/C/G/T)AC(A/G)TG(A/C/G/T)CC(A/G)CA(A/C/G/T)GG3' (SEQ ID NO:5). RT-PCR was performed using a RT-PCR kit from TakaRa under the following conditions: 94° C. for i minute, 42° C. for 1.5 minute, 72° C. for 1 min, for 40 cycles. Amplified fragments were blunted-end cloned into HincII site of ptz19, then sequenced. To obtain full-length SfIAP cDNAs, 5' RACE and 3' RACE were performed from Sf-21 nRNA using kits from Gibco BRL and TakaRa, respectively, and 5'CACTTGGTTTTGTCTCCCT-GACC3' (SEQ ID NO:6) and 5'ACTCAAAGTTGTG-TAAAATCTG3' (SEQ ID NO:7) as internal PCR-primers.

Example 2

Plasmid Constructions

A portion of the full-length SFIAP cDNA encompassing the complete open reading frame (ORF) was PCR-amplified and subcloned into the EcoRI-XhoI sites in pcDNA3-myc and pGEX4T-1 vectors for expression in mammalian cells as a myc-epitope tagged protein and in *E. coli* as a GST-fusion protein, respectively. The complete ORF of CpIAP was subcloned into the EcoRI-EcoRV sites of pcDNA3-myc or the EcoRI-SalI sites in pGEX4T-1. Plasmids encoding fragments of the SfIAP and CpIAP, including BIR1+2 (amino acid residues 1–323 for SfIAP, residues 1–220 for CpIAP) and RING (residues 324–377 for SfIAP and residues 221–275 for CpIAP) were amplified by PCR using primers containing either start or stop codons as appropriate and subcloned into pcDNA3-myc or pGEX4T-1 plasmids.

Example 3

Protein Expression and Purification pGEX4T-1-SfIAP and pGEX4T-1 -CpIAP plasmids were introduced into *E. coli* strain BL21 (DE3) containing the plasmid pT-Trx. GST fusion proteins were obtained by induction with 0.05 mM IPTG at 25° C. for 8 hours, then purified using glutathione-Sepharose, essentially as described (Deveraux, Q., Welsh, K. & Reed, J. *Methods of Enzymology* in press). Caspases-3, and -7, containing C-terminal His6-tags, and caspase-8 containing an N-terminal His6-tag were purified as described previously (Stennicke, H. R. & Salvesen, G. S. (I1997) *J. Biol. Chem.* 272, 25719–25723; Stennicke, H., et al., (1998) *J. Biol. Chem.* 273, 27084–27090; Stennicke, H., et al., (1999) *J. Biol. Chem.* 274, 8359–8362). Caspase-9 lacking the CARD domain (ΔCARD-caspase-9) was constructed by truncating the cDNA and introducing a start codon substituting Val139. The resulting cDNA was subcloned into pET-23b and expressed in BL21 (DE3), yielding fully processed enzyme when cells were induced using 0.2 mM IPTG at OD600=0.6 for 4 hrs (Stennicke, H., Deveraux, Q., Humike, E., Reed, J., Dixit, V. & Salvesen, G. (1999) *J. Biol. Chem.* 274, 8359–8362). All expressed caspases were purified by Ni-chelation affinity-chromatography, as described (Stennicke, H., et al., (1999) *J. Biol. Chem.* 274, 8359–8362; Stennicke, H. R. & Salvesen, G. S. (1997) *J. Biol. Chem.* 272, 25719–25723; Stennicke, H., et al., (1998) supra). Concentrations of purified enzymes were determined from absorbance at 280 nm based on the molar absorption coefficients: caspase-3 (A280=26,000M−1 cm−1), caspase-7 (A280=24,500 M−1 cm−1), caspase-9 (A280=30,010M−1 cm−1).

Example 4

Protein Binding Assay

[$^{35}$S]Pro-caspase-9 was in vitro transcribed and translated in the presence of [$^{35}$S]L-methionine using TNT kit from Promega. Protein were desalted and exchanged into buffer (20 mM HEPES pH 7.5, 10 mM KCl, 1.5 mM MgCl2, 1 mM EDTA and 1 mM DTT) with Bio-spin P-6 columns (Bio-Rad). GST-SfIAP, GST-CpIAP, GST-XIAP or GST-XIAPBIR1 (10 μg) immobilized on glutathione-Sepharose (5 μl) were incubated with in vitro-translated pro-caspase-9 (4 μl) in a total volume of 100 μl with caspase assay buffer (20 mM HEPES, pH7.4, 10% sucrose, 0.1% CHAPS, 1 mM EDTA, 100 mM NaCl). After incubation at 4 ° C. for 1 hour, beads were removed by centrifugation and washed twice with 0.5 ml of 50 mM Tris (pH 7.5), 150 mM NaCl, 2 mm DTT before analysis by SDS-PAGE and autoradiography.

Example 5

Enzyme Assays

Caspase activity was assayed by release of 7-amino-4-trifluoromethyl-coumarin (AFC) from Ac-DEVD or Ac-LEHD-containing synthetic peptides (Calbiochem) using continuous-reading instuments as described (Quan, L. T. et al., (1995) *J. Biol. Chem.* 270:10377–10379).

Example 6

Cell Extracts

Cytosolic extracts were prepared as described (Deveraux, Q., Takahashi, R., Salvesen, G. S. & Reed, J. C. (1997) *Nature* 388, 300–303) using human embryonic kidney (HEK) 293 cells. Cells were washed with ice-cold buffer A (20 mM HEPES pH 7.5, 10 mM KCl, 1.5 mM $MgCl_2$, 1 mM EDTA and 1 mM DTT), suspended in 1 volume of buffer A, incubated on ice for 20 mins, and then disrupted by 15 passages through a 26-gauge needle. Cell extracts were purified by centrifugation at 15000 g for 12 mins and supernatants were stored at −80 °C. For initiating caspase activation, either 100 nM of purified recombinant caspase-8 or 1 $\mu$M horse heart cytochrome c (Sigma) together with 1 mM dATP was added to extracts (Deveraux, Q. L., et al., (1998) *EMBO J.* 17, 2215–2223).

Example 7

Cell Culture, Transfections, and Apoptosis Assays

Insect Sf-21 cells were maintained at 27° C. in Excell 401 media (JHR Bioscience) supplemented with 2.5% fetal bovine serum. vP35del, containing a deletion in the p35 gene, was propagated in TN-368 cells (Clem, R. J., et al., (1991) *Science* 254, 1388–1390). Plasmids encoding full-length or deletion mutants of SfIAP (1 $\mu$g) were co-transfected with 1 $\mu$g vP35del viral DNA into Sf-21 cells using Lipofectin from Gibco. Occlusion body formation was observed under light microscopy 3 days post-transfection.

HEK293 and 293T cells were maintained in DMEM (Irvine Scientific) supplemented with 10% fetal bovine serum, 1 mM L-glutamine and antibiotics. 293 cells ($10^6$) were co-transfected using Superfect with 0.1 $\mu$g Green Fluoresence Protein (GFP) marker plasmid pEGFP (Clontech), 0.25 ug of either pcDNA3-Bax or pcDNA3-Fas, and 1.5 $\mu$g of either pcDNA3myc-SfIAP or pcDNA3myc-CpIAP. Alternatively, cells were co-transfected with 0.35 $\mu$g pcDNA3-caspase-9-Flag and 2.1 $\mu$g of either SfIAP or CpIAP. Both floating and adherent cells were recovered 24–36 hour post-transfection, pooled, and the percentage of GFP-positive cells that exhibited nuclear apoptotic morphology was determined by staining with 0.1 mg/ml DAPI (mean±S.D.) (Deveraux, Q., et al. (1997) *Nature* 388, 300–303; Deveraux, Q. L., et al., (1998) *EMBO J.* 17, 2215–2223; Roy, N., et al. (1997) *EMBO J.* 16, 6914–6925; Takahashi, R., et al. (1998) *J. Biol. Chem.* 273, 7787–7790). In some cases, lysates were prepared from transfected cells, normalized for total protein content, and analyzed by SDS-PAGE/immunoblotting as described (Deveraux, Q., et al., (1997) supra; Deveraux, Q. L., et al. (1998) supra; Roy, N. et al. (1997) supra; Takahashi, R., et al., (1998), supra.).

Example 8

Results of Cloning of SfIAP

RT-PCR was used to amplify a fragment of SfIAP from mRNA derived from Sf-21 cells. 5'RACE and 3'RACE were performed to obtain the full-length cDNA. The full-length SfLAP cDNA (SEQ ID NO:1) contains a continuous ORF (SEQ ID NO:2) encoding a protein of 377 amino acids (SEQ ID NO:3). This ORF is initiated by an AUG within a favorable context for translation and is preceded by upstream stop codons in all three reading frames. Similar to baculoviral IAPs, the predicted SfIAP contains two BIR domains, followed by a RING domain near its C-terminus. Within the BIR and RING regions, SfIAP shares 85% amino acid identity (90% similarity) with baculoviral CpIAP and 70% identity (80% similarity) with OpIAP. The sequence similarity between this cellular lepidopteran IAP and baculoviral IAPs suggests that baculoviral IAPs may have derived from host IAP genes.

Example 9

SfIAP Rescues AcNPV p35-deleted Virus in Sf-21 Cells

Previous studies showed that CpIAP and OpIAP require their BIR and RING domains to rescue AcMNPV p35-deleted virus in Sf cells (Clem, R. J. & Miller, L. K. (1994) *Mol. Cell. Biol.* 14, 5212–5222). SfIAP was tested to see if it also complements. p35-deficiency, preventing apoptosis by this mutant virus, thereby allowing its replication in insect cells. Plasmids containing full-length SfIAP or fragments of SfIAP comprising the two BIRs or the RING domain were co-transfected with AcMNPV p35 mutant viral DNA into Sf-21 cells. Cells were observed 72 hrs post-transfection. While full-length SfIAP complemented p35 deficiency, allowing replication of this mutant virus, as evidenced by occlusion body formation in Sf21cells, the BIR and RING truncation mutants of SfIAP failed to rescue in this assay. Thus, analogous to CpIAP and OpIAP, BIR and RING domains of SfIAP are required in combination for inhibition of apoptosis induced by AcMNPV p35 mutant virus.

Example 10

SfIAP and CpIAP Inhibit Bax-induced Not Fas-induced Apoptosis in Mammalian Cells Baculoviral IAPs have been reported to protect mammalian cells from some apoptotic stimuli (Hawkins, C. J. et al., (1996) *Proc. Natl. Acad. Sci. USA* 93, 13786–13790; Hawkins, C. et al., (1998) *Cell Death and Differentiation* 5, 569–576; Uren, A. G. et al., (1996) *Proc. Natl. Acad. Sci. USA* 93, 4974–4978). Tests were performed to determine whether SfIAP is also capable of functioning as an apoptosis suppressor in a mammalian cell context. For these experiments, apoptosis was induced in HEK293 cells by over-expression of either Fas or Bax—representing prototypical apoptotic stimuli which trigger alternative apoptosis pathways. The TNF-family receptor member Fas recruits pro-caspase-8 to receptor complexes and induces its activation. Caspase-8 then cleaves and activates caspase-3 and other downstream caspases that cause apoptosis. In contrast, Bax induces release of cytochrome c from mitochondria. Cytochrome c (cyto c) then binds Apaf-1, inducing recruitment of pro-caspase-9 to cytochrome c/Apaf-1 complexes and resulting in caspaes-9 activation. Active caspase-9 then cleaves and activates caspase-3 and other downstream caspases.

Plasmids encoding various IAPs were co-transfected with Bax or Fas into 293 cells and % apoptosis was determined 24–36 hours later. SfIAP, CpIAP and human XIAP inhibited Bax-induced apoptosis. In contrast, the BIR and RING truncation mutants of SfIAP and CpIAP failed to suppress apoptosis induced by Bax, as did the full-length IAP (OpIAP; AcIAP) from other baculovirus strains. Unlike Bax, SfIAP and CpIAP were ineffective at suppressing Fas-induced apoptosis in HEK293 cells (FIG. 2B), whereas XIAP did protect against Fas. Immunoblot analysis confirmed production of these various IAPs, excluding gross differences in the levels of these proteins as an explanation for the results. Thus, SfIAP and CpIAP are capable of inhibiting mammalian apoptosis pathways but they inhibit only a subset of the cell death pathways which are suppressed by their human counterpart, XIAP.

Example 11

Recombinant SfIAP and CpIAP Suppress Caspase Activation Induced by Cyto C in Vitro To further explore the mechanisms by which SfIAP and CpIAP inhibit mammalian apoptosis, a cell-free system in which exogenously added active caspase-8 or cyto c induces activation of caspase-3 and similar proteases, as measured by hydrolysis of Ac-DEVD-AFC (Quan, L. T. et al., (1995) *J. Biol. Chem.* 270, 10377–10379) was used. Caspase-8 and cyto c trigger the same apoptosis pathways in extracts which are activated by Fas and Bax in intact cells. In cell extracts treated with cyto c, recombinant SfIAP, CpIAP and XIAP completely blocked the hydrolysis of Ac-DEVD-AFC. A control protein consisting of the BIRI domain of XIAP did not interfere with caspase activity, demonstrating the specificity of these results. In contrast, recombinant SfIAP and CpIAP had no effect on DEVD-cleaving proteases in cell extracts treated with caspase-8.

Immunoblot analysis of caspase-3 processing confirmed the findings of protease assays. In cell extracts activated by cyto c or active caspase-8, ~33 kDa procaspase-3 was processed to yield 17–20 kDa forms of the large-subunit, indicative of active caspase-3 (the 12 kDa subunit of caspase-3 is undetectable with this anti-caspase-3 antibody). Recombinant SfIAP and CpIAP suppressed the processing of pro-caspase-3 in cyto c-treated but not in caspase-8-treated extracts, whereas XIAP suppressed in both cases. Taken together, these data suggest that SfIAP and CpIAP inhibit the caspase cascade activated by cyto c pathway at a step upstream of caspase-3 but do not suppress the cascade initiated by caspase-8.

Example 12

Grim Peptide Negatively Regulates SfIAP

It has been proposed that Drosophila apoptosis-inducers such as Grim function as negative regulators of IAPs (Deveraux, Q. & Reed, J. C. (1998) *Genes Dev.* 13, 239–252; Wang, S. et al. (1999) *Cell* 98, 453–463). The effects of a peptide corresponding to the IAP-binding domain of Grim (first 18 amino acid of Grim) were tested on SfIAP-mediated suppression of caspases in cyto c-stimulated cell extracts. While recombinant SfIAP was able to inhibit cyto c-induced activation of DEVD-cleaving caspases in cytosol extracts, addition of Grim peptide abrogated this inhibitory effect of SfIAP in a concentration-dependent manner, with a 5-fold excess of Grim peptide relative to SfIAPs resulting in complete restoration of caspase activity. In contrast, several control peptides of similar length had no effect. These results support the hypothesis that the fly apoptosis-inducer Grim is an inhibitor of *S. frugiperda* and baculoviral IAPs.

Example 13

SfIAP and CpIAP Directly Bind and Inhibit Mammalian Caspase-9

The observation that SfIAP and CpIAP suppress apoptosis induced by Bax and block caspase activation induced by cyto c suggested that these IAPs might inhibit caspase-9, the pinnacle caspase in the mitochondrial/cyto c pathway. To test this hypothesis, 293T cells were transfected with plasmids encoding pro-caspase-9 alone or in combination with SfIAP and CpIAP. Caspase activity and apoptosis were then assayed 24–36 hours later. Both SfIAP and CpIAP, as well as human XIAP (included as a positive control), markedly suppressed activation of downstream DEVD-cleaving caspases induced by overexpression of caspase-9 and also inhibited caspase-9-induced apoptosis. In contrast, OpIAP and AcIAP failed to suppress caspase activation or apoptosis, demonstrating the specificity of these results. Immunoblotting confirmed expression of all these IAP-family proteins at comparable levels. In contrast to full-length SfIAP and CpIAP, fragments of these IAPs containing only the BIR domains were unable to suppress activation of DEVD-cleaving caspases induced by overexpression of pro-caspase-9. Moreover, fragments of SfIAP and CpIAP containing only the RING domain enhanced rather than suppressing caspase activation and apoptosis induced by over-expression of pro-caspase-9.

To directly examine the possibility that SfIAP and CpLAP inhibit caspase-9, enzyme inhibition assays were performed using bacteria-produced recombinant active caspase-9, recombinant-purified SfIAP and CpIAP, and Ac-LEHD-AFC as a caspase-9 substrate. SfIAP and CpIAP inhibited recombinant active caspase-9 in a concentration-dependent manner. The molar-excess of SfIAP and CpIAP relative to caspase-9 which produced ~50% inhibition of protease activity was 8- and 12-fold respectively, similar to results reported previously for XIAP suppression of this member of the caspase family (Deveraux, Q. L. et al., (1998) *EMBO J.* 17, 2215–2223).

SfIAP and CpIAP also bound to caspase-9, as determined by experiments in which [$^{35}$S]-pro-caspase-9 was incubated with GST-SfIAP, GST-CpIAP, GST-XIAP and GST-XIAP-BIR1. Autoradiography showed that GST-SfIAP, GST-CpIAP and GST-XIAP associated with pro-caspase-9. In contrast, various control GST-fusion proteins, including XIAP-BIR1, failed to bind caspase-9, confirming the specificity of these results.

Unlike caspase-9, SfIAP and CpIAP neither bound nor inhibited recombinant purified caspases-3 and -7. In contrast, human XIAP was a potent inhibitor of caspases-3 and -7 in vitro, demonstrating that XIAP can inhibit a broader range of mammalian caspases than SfIAP and CpIAP.

Example 14

Production of Transgenic Plants

Transgenic tomato plants containing SfIAP were made by conventional techniques. Agrobacterium was used as a vehicle to introduce the heterologous gene into the plants.

All publications, patents, and patent applications cited in this specification are herein incorporated by reference as if each individual publication, patent, or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An isolated nucleic acid construct comprising a polynucleotide sequence of SEQ ID NO:1.

2. A host cell comprising a recombinant expression cassette comprising a promoter operably linked to a polynucleotide of SEQ ID NO:1.

3. A recombinant expression cassette comprising a polynucleotide sequence of SEQ ID NO:1.

4. An isolated nucleic acid construct comprising a polynucleotide sequence at least 95% identical to SEQ ID NO:1 and which encodes a protein that inhibits Bax-induced apoptosis in mammalian cells.

5. The isolated nucleic acid construct of claim 4, wherein the polynucleotide is SEQ ID NO:1.

6. A host cell comprising a recombinant expression cassette comprising a promoter operably linked to a polynucleotide at least 95% identical to SEQ ID NO:1 and which encodes a protein that inhibits Bax-induced apoptosis in mammalian cells.

7. The host cell of claim 6, wherein the polynucleotide is SEQ ID NO:1.

8. The host cell of claim 6, wherein the promoter is inducible.

9. The host cell of claim 6, wherein the promoter is constitutive.

10. The host cell of claim 6, which is an insect cell.

11. The host cell of claim 6, which is a plant cell.

12. A recombinant expression cassette comprising a polynucleotide sequence at least 95% identical to SEQ ID NO:1 and which encodes a protein that inhibits Bax-induced apoptosis in mammalian cells.

13. The recombinant expression cassette of claim 12, wherein the polynucleotide sequence is SEQ ID NO:1.

14. The recombinant expression cassette of claim 12, wherein the promoter is inducible.

15. The recombinant expression cassette of claim 12, wherein the promoter is constitutive.

16. A recombinant baculovirus comprising a nucleic acid of claim 4.

17. A transgenic plant comprising a nucleic acid of claim 4.

* * * * *